(12) United States Patent
Lee et al.

(10) Patent No.: US 11,986,276 B2
(45) Date of Patent: May 21, 2024

(54) BIOSENSOR AND BIOSENSOR ARRAY AND DEVICE

(71) Applicant: Samsung Electronics Co., Ltd., Suwon-si (KR)

(72) Inventors: Gae Hwang Lee, Seongnam-si (KR); Hyun Bum Kang, Yongin-si (KR); Jong Won Chung, Hwaseong-si (KR); Youngjun Yun, Yongin-si (KR); Yeongjun Lee, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 271 days.

(21) Appl. No.: 17/079,868

(22) Filed: Oct. 26, 2020

(65) Prior Publication Data
US 2021/0378533 A1    Dec. 9, 2021

(30) Foreign Application Priority Data

Jun. 5, 2020   (KR) ........................ 10-2020-0068623

(51) Int. Cl.
*A61B 5/024*   (2006.01)

(52) U.S. Cl.
CPC ...... *A61B 5/02427* (2013.01); *A61B 5/02438* (2013.01); *A61B 2562/0238* (2013.01)

(58) Field of Classification Search
CPC ........ A61B 2562/0238; A61B 5/02438; A61B 5/02427
See application file for complete search history.

(56) References Cited

U.S. PATENT DOCUMENTS

| | | | | |
|---|---|---|---|---|
| 4,938,218 | A | * | 7/1990 | Goodman ............. A61B 5/252 600/338 |
| 9,861,315 | B2 | | 1/2018 | Gretz et al. |
| 2009/0156912 | A1 | | 6/2009 | Kuhn et al. |
| 2011/0260176 | A1 | * | 10/2011 | Onoe ................... A61B 5/0261 438/33 |
| 2013/0120760 | A1 | * | 5/2013 | Raguin ................. A61B 5/117 356/612 |
| 2014/0051955 | A1 | * | 2/2014 | Tiao .................... A61B 5/14552 600/323 |
| 2014/0151586 | A1 | * | 6/2014 | Shimuta ............. A61B 5/14551 250/578.1 |

(Continued)

FOREIGN PATENT DOCUMENTS

| | | | | |
|---|---|---|---|---|
| CN | 107123723 A | * | 9/2017 | ............. G02B 5/208 |
| KR | 100681387 B1 | | 2/2007 | |

(Continued)

OTHER PUBLICATIONS

Translation of WO2020121989 (Year: 2020).*
Extended European Search Report dated Apr. 13, 2021 for corresponding European Application No. 20205327.8.

*Primary Examiner* — Ashley K Buran
*Assistant Examiner* — Helene Bor
(74) *Attorney, Agent, or Firm* — Harness, Dickey & Pierce, P.L.C.

(57) ABSTRACT

Disclosed is a biosensor including a light-emitting element, a photo-detective element, a light transmitting layer under the light-emitting element and the photo-detective element, and an optical structure inside the light transmitting layer and configured to control a propagation direction of light, a biosensor array and a device.

19 Claims, 19 Drawing Sheets

(56) References Cited

U.S. PATENT DOCUMENTS

| | | | |
|---|---|---|---|
| 2017/0000350 A1* | 1/2017 | Kwon | A61B 5/02427 |
| 2017/0311856 A1 | 11/2017 | Lasarov | |
| 2018/0132771 A1 | 5/2018 | Li et al. | |
| 2019/0133470 A1 | 5/2019 | Szabados | |
| 2019/0192004 A1* | 6/2019 | Matsuo | A61B 5/681 |
| 2020/0000345 A1* | 1/2020 | Connor | A61B 5/4875 |
| 2021/0335951 A1* | 10/2021 | Wang | H01L 25/50 |

FOREIGN PATENT DOCUMENTS

| | | | |
|---|---|---|---|
| KR | 101593923 B1 | 2/2016 | |
| KR | 10-2019-0006655 A | 1/2019 | |
| KR | 101987399 B1 | 6/2019 | |
| KR | 102034350 B1 | 11/2019 | |
| KR | 102051440 B1 | 12/2019 | |
| WO | WO-2018/112401 A1 | 6/2018 | |
| WO | WO-2020121989 A1 * | 6/2020 | G01S 7/481 |

* cited by examiner

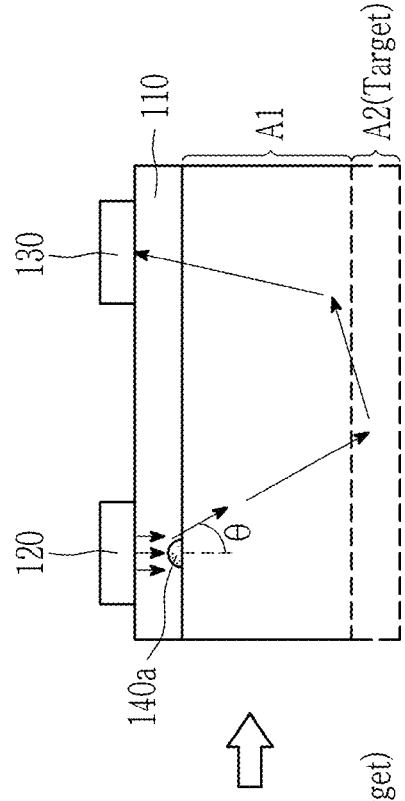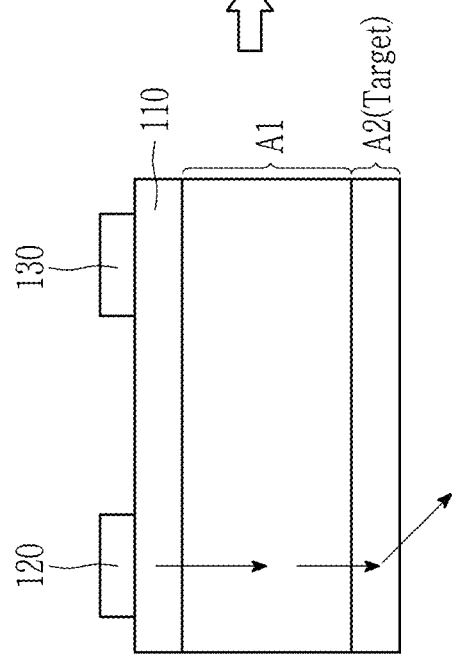

BIOSENSOR AND BIOSENSOR ARRAY AND DEVICE

CROSS-REFERENCE TO RELATED APPLICATION

This application claims priority to and the benefit of Korean Patent Application No. 10-2020-0068623 filed in the Korean Intellectual Property Office on Jun. 5, 2020, the entire contents of which are incorporated herein by reference.

BACKGROUND

1. Field

A biosensor, a biosensor array, and a device are disclosed.

2. Description of the Related Art

Recently, studies on skin-attachable devices for directly attaching to skin or clothing to obtain bio-information have been conducted. Such skin-attachable devices include a biosensor for obtaining bio-information. For example, a photoplethysmography (PPG) sensor may obtain a PPG signal from a user, and by analyzing the PPG signal, bio-information such as a user's blood pressure, arrhythmia, heart rate, and/or oxygen saturation may be obtained.

SUMMARY

Some example embodiments provide a biosensor with improved performance.

Some example embodiments provide a biosensor array including the biosensor.

Some example embodiments provide a device including the biosensor or the biosensor array.

According to some example embodiments, provided is a biosensor including a light-emitting element, a photo-detective element, a light transmitting layer under the light-emitting element and the photo-detective element, and an optical structure inside the light transmitting layer and configured to control a propagation direction of light.

The optical structure may control a propagation direction of light emitted from the light-emitting element or a propagation direction of light reflected by a living body.

The optical structure may include a first optical structure disposed to overlap the light-emitting element in a thickness direction of the light transmitting layer.

The first optical structure may be configured to scatter or refract light emitted from the light-emitting element.

The first optical structure may control light emitted in a substantially vertical direction with respect to an in-plane direction of the light-emitting element to travel the light at an angle of greater than or equal to about 10 degrees with respect to a vertical direction of the light-emitting element.

The first optical structure may include a microlens or a microlens array.

An area of the microlens or the microlens array may be smaller than or equal to an area of the light-emitting element.

A refractive index of the material constituting the first optical structure may be different from a refractive index of the material constituting the light transmitting layer.

The first optical structure may have pores.

The first optical structure may be configured to reflect light emitted from the light-emitting element.

The first optical structure may be controlled to reflect light emitted from the light-emitting element and to travel the reflect light at an angle of less than about 60 degrees with respect to a vertical direction of the light-emitting element.

The first optical structure may have a cylindrical or truncated circular conical shape.

The first optical structure may include a metal.

The first optical structure may control light emitted from the light-emitting element to travel the light at an angle of greater than or equal to about 10 degrees and less than about 60 degrees with respect to a vertical direction of the light-emitting element.

The optical structure may further include a second optical structure disposed to overlap the photo-detective element in a thickness direction of the light transmitting layer.

The optical structure may further include a third optical structure between the light-emitting element and the photo-detective element.

The third optical structure may be configured to scatter or refract light reflected by the living body to lead the scattered or refracted light to the photo-detective element.

The third optical structure may include a plurality of nanoparticles or porous structures.

The optical structure may further include a second optical structure disposed to overlap the photo-detective element in a thickness direction of the light transmitting layer.

The light transmitting layer may include a stretchable material.

The light transmitting layer may include a plurality of first regions having a high elastic modulus and a second region having a lower elastic modulus than the first region, the second region being disposed between the adjacent first regions, and each of the light-emitting element and the photo-detective element may be disposed on the first region.

According to some example embodiments, a biosensor array including the biosensors is provided.

The biosensor array may include a plurality of unit elements, and each unit element may include one or more light-emitting elements and one or more photo-detective elements.

Each unit element may further include a pressure sensor.

According to some example embodiments, a device including the biosensor or the biosensor array is provided.

The device may be a patch-typed skin-attachable device or a band-typed skin-attachable device.

A performance of the biosensor may be improved.

DETAILED DESCRIPTION

Figure 1:
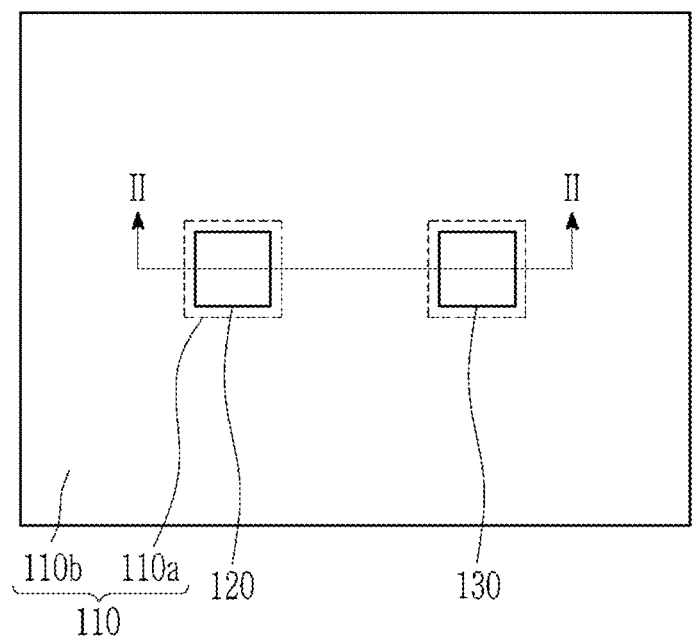
FIG. 1 is a top plan view showing an example of a biosensor according to some example embodiments.

Hereinafter, example embodiments are described in detail so that those skilled in the art can easily implement them. However, the actual applied structures may be implemented in various different forms and is not limited to the implementations described herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements present.

Hereinafter, a biosensor according to example embodiments is described.

The biosensor is a sensor for detecting bio-information through a biological signal, such as a photoplethysmography (PPG) sensor, a blood pressure (BP) sensor, a blood glucose (BG) sensor, and/or a near infrared brain imaging sensor, but is not limited thereto. For example, the biosensor may be a photoplethysmography (PPG) sensor that detects changes in blood flow of blood vessels.

Figure 2:
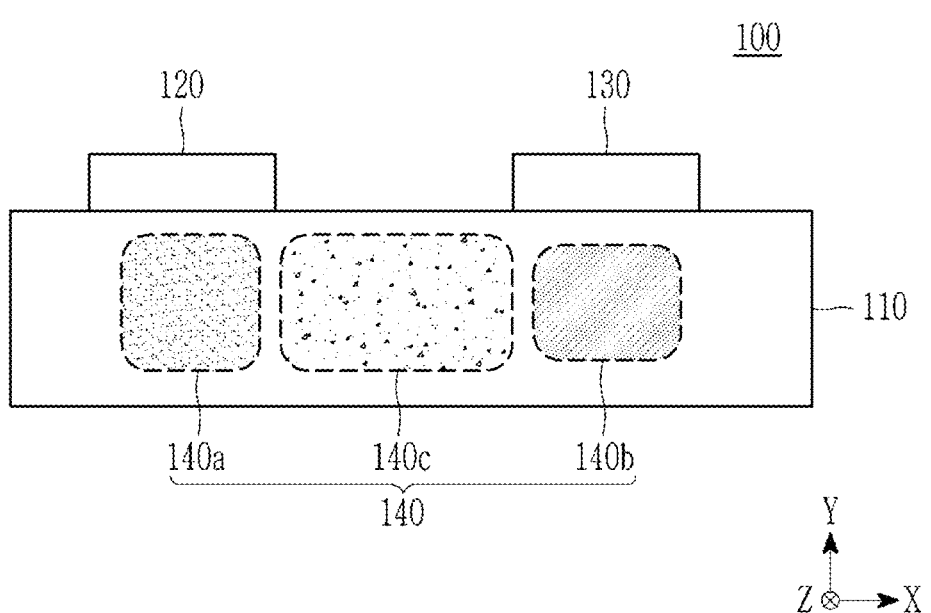
FIG. 2 is a cross-sectional view of the biosensor of FIG. 1 taken along line II-II.

FIG. 1 is a top plan view showing an example of a biosensor according to some example embodiments, and FIG. 2 is a cross-sectional view of the biosensor of FIG. 1 taken along line II-II.

Referring to FIGS. 1 and 2, a biosensor 100 according to some example embodiments includes a light transmitting layer 110, a light-emitting element 120, a photo-detective element 130, and/or an optical structure 140.

The light transmitting layer 110 may be disposed under light-emitting element 120 and the photo-detective element 130 to support the light-emitting element 120 and the photo-detective element 130. The light transmitting layer 110 may be, for example, a support substrate or may be formed on a separate support substrate (not shown). When a separate support substrate is included, the support substrate may be a stretchable substrate.

The light transmitting layer 110 may be configured to transmit light, and may have for example, light transmittance of greater than or equal to about 70%, greater than or equal to about 75%, greater than or equal to about 80%, greater than or equal to about 85%, greater than or equal to about 90%, greater than or equal to about 95%, greater than or equal to about 97%, greater than or equal to about 98%, or greater than or equal to about 99%. The light transmitting layer 110 may be disposed in a direction in which light is emitted from the light-emitting element 120 and in a direction in which light is flowed into the photo-detective element 130. For example, the light transmitting layer 110 may be disposed closer to the living body (skin, blood vessel) to be detected in the light-emitting element 120 and the photo-detective element 130.

The light transmitting layer 110 may be a stretchable layer, and thus may respond flexibly depending to external forces or external movements such as twisting, pressing or stretching, and may be easily restored to its original state. The light transmitting layer 110 may include a stretchable material such as an elastomer, and the stretchable material may include an organic elastomer, an organic/inorganic elastomer, an inorganic elastomer-like material, or a combination thereof. The organic elastomer or the organic/inorganic elastomer may be, for example, substituted or unsubstituted polyorganosiloxane such as polydimethylsiloxane, an elastomer including substituted or unsubstituted butadiene moiety such as styrene-ethylene-butylene-styrene, an elastomer including a urethane moiety, an elastomer including an acrylic moiety, an elastomer including an olefin moiety, or a combination thereof, but is not limited thereto. The inorganic elastomer-like material may include an elastic ceramic, solid metal, liquid metal, or a combination thereof, but is not limited thereto.

The light transmitting layer 110 may include regions having different stiffness, for example, a first region 110a having relatively high stiffness and a second region 110b having a relatively low stiffness than the first region 110a. Herein, the stiffness indicates a degree of resistance to deformation when a force is applied from the outside. Relatively high stiffness means that the resistance to deformation is relatively large, so that deformation is small while relatively low stiffness means that the resistance to deformation is relatively small, so that the deformation is large.

The stiffness may be evaluated from an elastic modulus, and a relatively high elastic modulus may mean relatively high stiffness and a relatively low elastic modulus may mean a relatively low stiffness. The elastic modulus may be, for example, a Young's modulus. A difference between elastic moduli of the first region 110a and the second region 110b of the light transmitting layer 110 may be about 100 times or more, and the elastic modulus of the first region 110a may be about 100 times higher than the elastic modulus of the second region 110b. The difference between the elastic modulus of the first region 110a and the second region 110b may be about 100 to 100,000 times within the above range, and the elastic modulus of the first region 110a may be about 100 times to about 100,000 times higher than the elastic modulus of the second region 110b, but is not limited thereto. For example, the elastic modulus of the first region 110a may be about $10^7$ Pa to about $10^{12}$ Pa, and the elastic modulus of the second region 110b may be greater than or equal to about $10^2$ Pa and less than about $10^7$ Pa, but is not limited thereto.

Elongation rates of the first region 110a and the second region 110b of the light transmitting layer 110 may be different due to the aforementioned difference in stiffness, and the elongation rate of the second region 110b may be higher than the elongation rate of the first region 110a. Herein, the elongation rate may be a percentage of the length change that is increased to a breaking point with respect to the initial length. For example, the elongation rate of the first region 110a of the light transmitting layer 110 may be less than or equal to about 5%, within the range, about 0% to about 5%, about 0% to about 4%, about 0% to about 3%, about 0% to about 2%, about 0% to about 1%, about 0.5% to about 5%, about 0.5% to about 4%, about 0.5% to about 3%, about 0.5% to about 2%, or about 1% to about 2%. For example, the elongation rate of the second region 110b of the light transmitting layer 110 may be greater than or equal to about 10%, within the range, about 10% to about 300%, about 10% to about 200%, about 10% to about 100%, about 10% to about 90%, about 10% to about 80%, about 10% to about 70%, about 10% to about 60%, about 10% to about 50%, about 10% to about 40%, about 20% to about 70%, about 20% to about 60%, about 20% to about 50%, or about 20% to about 40%.

The plurality of first regions 110a of the light transmitting layer 110 may have an island-shape separated from each other, and the light-emitting element 120 and the photo-detective element 130 which are described later are disposed on each first region 110a of the light transmitting layer 110.

The second region 110b of the light transmitting layer 110 may be a region other than the plurality of first regions 110a and may be continuously connected throughout. The second region 110b of the light transmitting layer 110 may be a region providing stretchability and due to its relatively low stiffness and high elongation rate, it may flexibly respond to external forces or external movements such as twisting, pressing or stretching, and may be easily restored to its original state.

For example, the first region 110a and the second region 110b of the light transmitting layer 110 may have different shapes. For example, the first region 110a of the light transmitting layer 110 may be flat and the second region 110b may include a two-dimensional or three-dimensional stretchable structure. The two-dimensional or three-dimensional stretchable structure may have, for example, a wavy shape, a wrinkle shape, a popup shape, or a non-coplanar mesh shape, but is not limited thereto.

For example, the first region 110a and the second region 110b of the light transmitting layer 110 may include different materials. For example, the first region 110a of the light transmitting layer 110 may include an inorganic material, an organic material, and/or an organic/inorganic material having relatively high stiffness and a low elongation rate, and the second region 110b of the light transmitting layer 110 may include an inorganic material, an organic material, and/or an organic/inorganic material having a relatively low stiffness and high elongation rate. For example, the first region 110a of the light transmitting layer 110 may include an organic material such as polycarbonate, polymethylmethacrylate, polyethyleneterephthalate, polyethylenenaphthalate, polyimide, polyamide, polyamideimide, polyethersulfone, or a combination thereof, a carbon structure such as diamond carbon, and the second region 110b of the light transmitting layer 110 may include an organic or organic/inorganic elastomer such as a substituted or unsubstituted polyorganosiloxane such as polydimethylsiloxane, an elastomer including a substituted or unsubstituted butadiene moiety such as styrene-ethylene-butylene-styrene, an elastomer including a urethane moiety, an elastomer including an acrylic moiety, an elastomer including an olefin moiety, or a combination thereof; an inorganic elastomer-like material such as ceramic, a solid metal, a liquid metal, or a combination thereof, but they are not limited thereto.

For example, the first region 110a and the second region 110b of the light transmitting layer 110 may be formed with the same material, and may have different stiffness by different conditions such as polymerization degrees and/or curing degrees. For example, the light transmitting layer 110 may have the first region 110a having a relatively high stiffness and the second region 110b having a relatively low stiffness which are formed by varying the polymerization degrees, types and contents of curing agents, and/or curing temperatures, based on polydimethylsiloxane.

As described above, the light transmitting layer 110 includes a first region 110a having a relatively high stiffness and a low elongation rate, and a second region 110b having a relatively low stiffness and a high elongation rate, and the light-emitting element 120 and the photo-detective element are disposed on the first region 110a of the light transmitting layer 110, and thereby even when a large external force or movement is applied to the light transmitting layer 110, the light-emitting element 120 and photo-detective element 130 disposed on the first region 110a of the light transmitting layer 110 receive relatively less strain and thus, the light-emitting element 120 and photo-detective element 130 are reduced or prevented from being damaged or destroyed by excessive strain.

The light-emitting element 120 may be configured to emit light in a predetermined or alternatively, desired wavelength region, and may include, for example, an inorganic light emitting diode, an organic light emitting diode, or a micro light emitting diode. The light-emitting element 120 may include, for example, a pair of electrodes and a light emitting layer disposed between the pair of electrodes. For example, one of the pair of electrodes may be a light-transmitting electrode and the other may be a reflecting electrode, for example, an electrode disposed close to the light transmitting layer 110 may be a light-transmitting electrode. For example, the pair of electrodes may be stretchable electrodes, and the stretchable electrodes may include, for example, a stretchable conductor, or may have a stretchable shape such as a wavy, wrinkled, pop-up, or non-planar mesh shape. For example, the light emitting layer may include an organic light emitting material, a quantum dot, and/or perovskite, but is not limited thereto. The light emitting layer may be configured to emit light in one of the wavelength regions of a blue wavelength region, a green wavelength region, a red wavelength region, and an infrared wavelength region, for example, light in one of the wavelength regions of a green wavelength region, a red wavelength region, and an infrared wavelength region, for example light in a green wavelength region. The pair of electrodes may be stretchable electrodes, and the light emitting layer may be a stretchable light emitting layer, and accordingly, the light-emitting element 120 may be, for example, a stretchable element.

The photo-detective element 130 may be configured to absorb light in a predetermined or alternatively, desired wavelength region, and may include, for example, an inorganic photodiode or an organic photoelectric conversion element. The photo-detective element 130 may include, for example, a pair of electrodes and a photoelectric conversion layer between the electrodes. For example, one of the pair of electrodes may be a light-transmitting electrode and the other may be a reflecting electrode, for example, an electrode disposed close to the light transmitting layer 110 may be a light-transmitting electrode. For example, the pair of electrodes may be stretchable electrodes, and the stretchable electrodes may include, for example, a stretchable conductor, or may have a stretchable shape such as a wavy, wrinkled, pop-up, or non-planar mesh shape. As an example, the photoelectric conversion layer may include, for example, an inorganic semiconductor, an organic semiconductor, and/or an organic/inorganic semiconductor, and may include, for example, a p-type semiconductor and an n-type semiconductor forming a pn junction. As an example, the photoelectric conversion layer may be a stretchable photoelectric conversion layer. The photo-detective element 130 may be, for example, a stretchable element.

The light emitted from the light-emitting element 120 may pass through the light transmitting layer 110 and be reflected by the target portion (hereinafter referred to as a 'target') of a living body such as a blood vessel, and the reflected light pass through the light transmitting layer 110 again and may be absorbed in the photo-detective element 130 to obtain a biological signal.

The optical structure 140 may be disposed inside the light transmitting layer 110 and control a light propagation direction by, for example, scattering, refracting, and/or reflecting light that passes through the light transmitting layer 110. The light of which propagation direction is controlled by the optical structure 140 may effectively reach a target such as a blood vessel or the photo-detective element 130.

For example, the optical structure 140 may control the propagation direction of light emitted from the light-emitting element 120 so that the light may effectively reach the target. Accordingly, the light emitted from the light-emitting element 120 may not reach the target or pass through the target as it is, thereby reducing lost light.

For example, the optical structure 140 may control the propagation direction of light flowed into the photo-detective element 130. The light flowed into the photo-detective element 130 may be, for example, light reflected by the target. Accordingly, it is possible to reduce non-detection and loss of light due to the fact that the light reflected by the target proceeds to an area other than the photo-detective element 130.

Referring to FIG. 2, the optical structure 140 may include a first optical structure 140a overlapped with the light-emitting element 120 in the thickness direction (e.g., the Y direction) of the light transmitting layer 110, a second optical structure 140b overlapped with the photo-detective element 130 in the thickness direction (e.g., the Y direction) of the light transmitting layer 110, and/or a third optical structure 140c disposed between the light-emitting element 120 and the photo-detective element 130, from which at least one may be selected and included in the optical structure 140. In FIG. 2, the first, second, and third optical structures 140a, 140b, and 140c are shown to have a predetermined or alternatively, desired shape and size in order to explain disposition relationship with the light-emitting element 120 and the photo-detective element 130, but are not limited thereto.

For example, the optical structure 140 may control a propagation direction of light emitted in a substantially vertical direction among light emitted from the light-emitting element 120. This will be illustrated referring to FIGS. 3 to 5.

Figure 3:
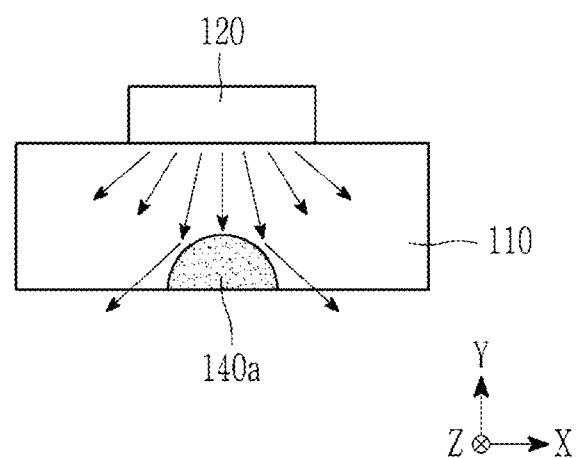
FIG. 3 is an enlarged schematic view showing an example of a portion of a light-emitting element of the biosensor of FIG. 2, FIGS. 4A and 4B are schematic views showing an example of an optical structure in the biosensor of FIG. 3, FIGS. 5A and 5B are schematic views showing an example of a propagation direction of light in the biosensor of FIG. 3.
Figure 4B:
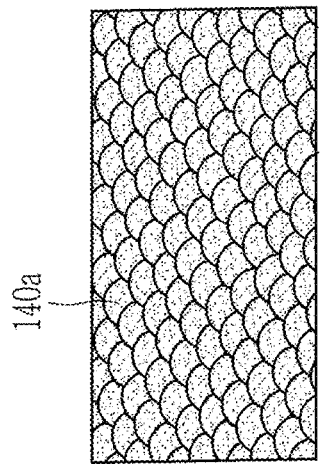
Figure 4A:
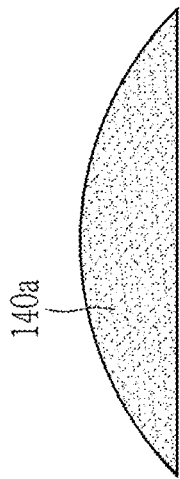

FIG. 3 is an enlarged schematic view showing an example of a portion of a light-emitting element of the biosensor of FIG. 2, FIGS. 4A and 4B are schematic views showing an example of an optical structure in the biosensor of FIG. 3, and FIGS. 5A and 5B are schematic views showing an example of a propagation direction of light in the biosensor of FIG. 3.

Referring to FIG. 3, the first optical structure 140a is overlapped with the light-emitting element 120 in the thickness direction (e.g., the Y direction) of the light transmitting layer 110 and may be configured to scatter or refract the light emitted in a substantially vertical direction with respect to the in-plane direction (e.g., the X direction) of the light-emitting element 120 and thus change the propagation direction of the light. For example, the first optical structure 140a may be configured to scatter or refract the light emitted in a substantially vertical direction with respect to the in-plane direction (e.g., the X direction) of the light-emitting element 120 to travel obliquely.

The first optical structure 140a may have a shape capable of causing such scattering or refraction. For example, the first optical structure 140a may include a hemisphere-shaped microlens shown in FIG. 4A or a microlens array shown in FIG. 4B. A diameter of the microlens may be several micrometers to several hundred micrometers, for example, greater than or equal to about 1 μm and less than about 1000 μm, about 1 μm to about 800 μm, about 10 μm to about 700 μm, about 20 μm to about 600 μm, or about 30 μm to about 500 μm, but is not limited thereto. For example, the microlens or microlens array may have a smaller or equal area than that of the light-emitting element 120, for example, about 0.1 times to about 1 time, about 0.2 times to 1 time, about 0.3 times to about 1 time, about 0.4 times to about 1 time, about 0.5 times to about 1 time, about 0.1 times to about 0.9 times, about 0.2 times to about 0.9 times, or about 0.3 times to about 0.9 times compared with that of the light-emitting element 120. Accordingly, the propagation direction of the substantially vertically incident light from the light-emitting element 120 may be effectively changed.

The first optical structure 140a may include a material causing this scattering or refraction, and the material of the first optical structure 140a may have a different refractive index from that of a material of the light transmitting layer 110.

For example, the refractive index of the material of the first optical structure 140a may be higher than that of the material of the light transmitting layer 110 and, for example, greater than or equal to about 0.1 or greater than or equal to about 0.2 higher than that of the material of the light transmitting layer 110. For example, the first optical structure 140a may include an organic material, an inorganic material, an organic/inorganic material, or a combination thereof, which satisfies this refractive index, for example, an organic material, an inorganic material, or an organic/inorganic material, or a combination thereof, which has a relatively high refractive index of greater than or equal to about 1.5, greater than or equal to about 1.6, greater than or equal to about 1.8, or greater than or equal to about 2.0. For example, the first optical structure 140a may be formed of a photosensitive polymer having a relatively high refractive index.

For example, the refractive index of the material constituting the first optical structure 140a may be lower than that of the material constituting the light transmitting layer 110, for example, greater than or equal to about 0.1 or greater than or equal to about 0.2 lower than that of the material constituting the light transmitting layer 110. For example, the first optical structure 140a may include an organic material, an inorganic material, an organic/inorganic material, or a combination thereof that satisfies the refractive index. For example, the first optical structure 140a may include an organic material, an inorganic material, an organic/inorganic material, or a combination thereof having a refractive index of less than about 1.4, less than or equal to about 1.3, less than or equal to about 1.2, or less than or equal to about 1.1 and may have, for example, pores including air having a refractive index of about 1.0.

As shown in FIG. 5A, when there is no first optical structure 140a, the light emitted in a substantially vertical direction with respect to the in-plane direction (e.g., the X direction) of the light-emitting element 120 may substantially vertically enter a skin A1 and a target A2 such as a blood vessel, and the vertically incident light just passes the target A2 such as a blood vessel and is not reflected but lost in the living body. This light loss may deteriorate efficiency of the biosensor.

Referring to FIG. 5B, the first optical structure 140a is disposed where light emitted from the light-emitting element 120 and thus may pass and scatter or refract light emitted in the vertical direction (e.g., the Y direction) of the light-emitting element 120, to change the propagation direction of light emitted at a low angle of about 0° to about 10° with the vertical direction of the light-emitting element 120 into an angle (8) of greater than or equal to about 10°, for example, greater than or equal to about 15°, greater than or equal to about 20°, greater than or equal to about 25°, about 10° to about 70°, about 10° to about 65°, about 10° to about 60°, greater than about 10° to less than about 60°, about 15° to about 70°, about 15° to about 65°, about 15° to about 60°, about 20° to about 70°, about 20° to about 65°, about 20° to about 60°, about 25° to about 70°, about 25° to about 65°, or about 25° to about 60° with respect to the vertical direction (e.g., the Y direction) of the light-emitting element 120.

Accordingly, the light having the propagation direction changed by the first optical structure 140a may obliquely flow into the skin A1 and be effectively reflected by the target A2 such as a blood vessel, and as shown in FIG. 5A, light not reflected but lost in the living body may be effectively reduced.

For another example, the optical structure 140 may control the propagation direction of light emitted in the substantially parallel direction out of the light emitted from the light-emitting element 120. This will be explained referring to FIGS. 6 to 8.

Figure 6:
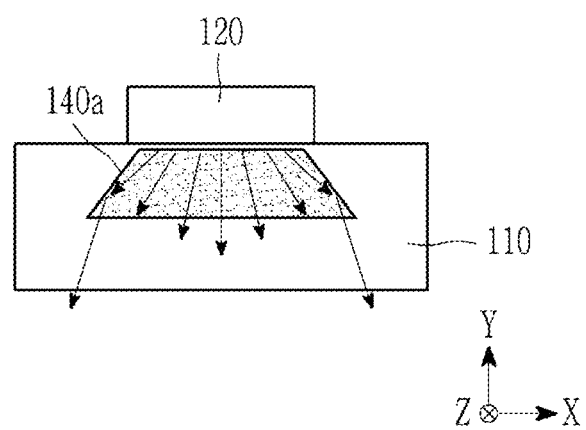
FIG. 6 is an enlarged schematic view showing another example of a portion of a light-emitting element of the biosensor of FIG. 2, FIGS. 7A and 7B are schematic views showing an example of an optical structure in the biosensor of FIG. 6, FIGS. 8A and 8B are schematic views showing another example of a propagation direction of light in the biosensor of FIG. 6.
Figure 7B:
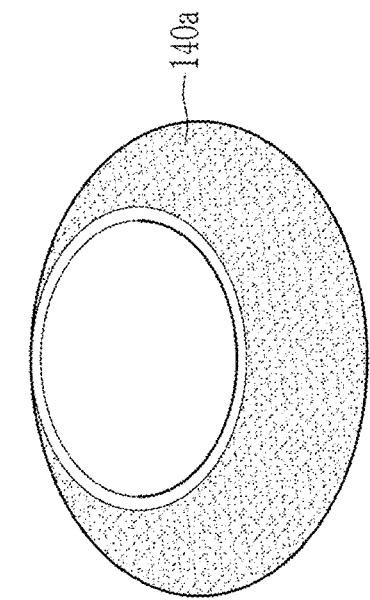
Figure 7A:
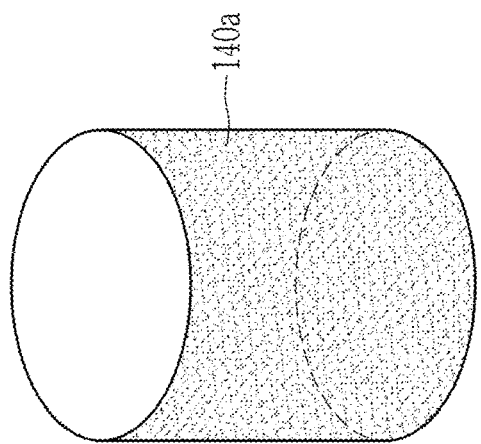
Figure 8A:
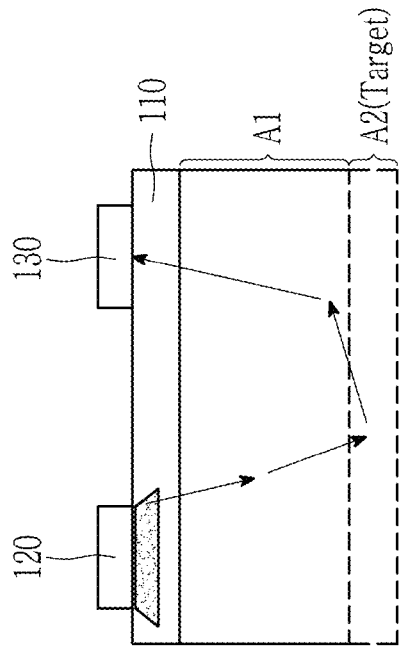
Figure 8B:
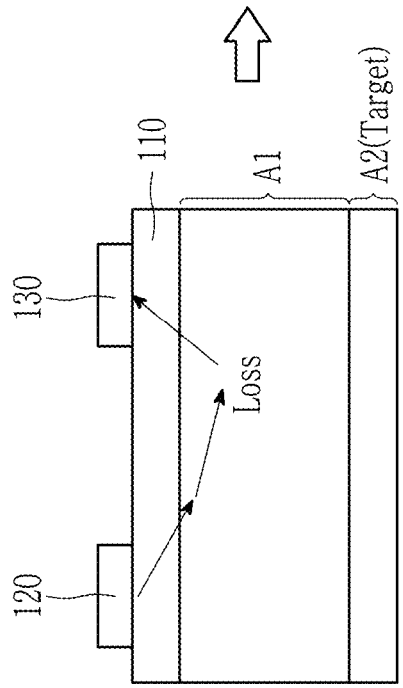

FIG. 6 is an enlarged schematic view showing another example of a light-emitting element portion of the biosensor of FIG. 2, FIGS. 7A and 7B are schematic views showing an example of an optical structure in the biosensor of FIG. 6, and FIGS. 8A and 8B are schematic views showing another example of a propagation direction of light in the biosensor of FIG. 6.

Referring to FIG. 6, the first optical structure 140a is overlapped with the light-emitting element 120 in the thickness direction (e.g., the Y direction) of the light transmitting layer 110 and thus may be configured to reflect light emitted at an excessively high angle with respect to the vertical direction (e.g., the Y direction) of the light-emitting element 120 and change the propagation direction of the light into a lower angle than that. For example, the first optical structure 140a may be configured to reflect the light emitted at a high angle of greater than or equal to about 70° with respect to the vertical direction (e.g., the Y direction) of the light-emitting element 120 into an angle of less than about 60° with respect to the vertical direction (e.g., the Y direction) of the light-emitting element 120.

The first optical structure 140a may have a shape causing this reflection. For example, the first optical structure 140a may have a cylindrical shape shown in FIG. 7A or a truncated circular cone shape shown in FIG. 7B. A diameter (e.g., a major axis) and a height of the cylinder or truncated circular cone may be respectively several micrometers to hundreds of micrometers, for example, greater than or equal to about 1 μm and less than about 1000 μm, about 1 μm to about 800 μm, about 10 μm to about 700 μm, about 20 μm to about 600 μm, or about 30 μm to about 500 μm, but are not limited thereto. The first optical structure 140a may be internally hollow. For example, the cylinder or truncated circular cone may have a larger area than that of the light-emitting element 120 and accordingly, may effectively be configured to reflect incident light at an excessively high angle with respect to the vertical direction (e.g., the Y direction) of the light-emitting element 120.

The first optical structure 140a may include a material causing this reflection, for example, a metal. For example, the first optical structure 140a may be formed of the metal, or coated with the metal on the surface.

As shown in FIG. 8A, when there is no first optical structure 140a, the light emitted at an excessively high angle with respect to the vertical direction (e.g., the Y direction) of the light-emitting element 120 may not reach the target A2 such as a blood vessel but be lost in the skin A1 or the light transmitting layer 110 or change its propagation direction and flow into the photo-detective element 130. This light may not include bio-information and thus deteriorate efficiency of the biosensor 100.

Referring to FIG. 8B, the first optical structure 140a is disposed where light emitted from the light-emitting element 120 passes and thus may be configured to reflect light emitted at a high angle of greater than or equal to about 70°, for example, in the vertical direction (e.g., Y direction) of the light-emitting element 120 and change the propagation direction of the light into an angle of less than about 60°, less than or equal to about 55°, less than or equal to about 50°, less than or equal to about 45°, less than or equal to about 40°, greater than or equal to about 10° and less than about 60°, about 10° to about 55°, about 10° to about 50°, about 10° to about 45°, about 10° to about 40°, greater than or equal to about 15° and less than 60°, about 15° to about 55°, about 15° to about 50°, about 15° to about 45°, about 15° to about 40°, greater than or equal to about 20° and less than about 60°, about 20° to about 55°, about 20° to about 50°, about 20° to about 45°, about 20° to about 40°, greater than or equal to about 25° and less than about 60°, about 25° to about 55°, about 25° to about 50°, about 25° to about 45°, or about 25° to about 40° with respect to the vertical direction (e.g., the Y direction) of the light-emitting element 120.

Accordingly, the light having a propagation direction changed by the first optical structure 140a obliquely flows into the skin A1 and may be effectively reflected by the target A2 such as a blood vessel. Accordingly, the first optical structure 140a may effectively reduce light not reaching the target A2 such as a blood vessel but lost or having no bio-information and thus improve efficiency of the biosensor 100.

As another example, the optical structure 140 may control a direction in which light is flowed into the photo-detective element 130, for example, light reflected by the target A2. This will be described with reference to FIGS. 9 and 10.

Figure 9:
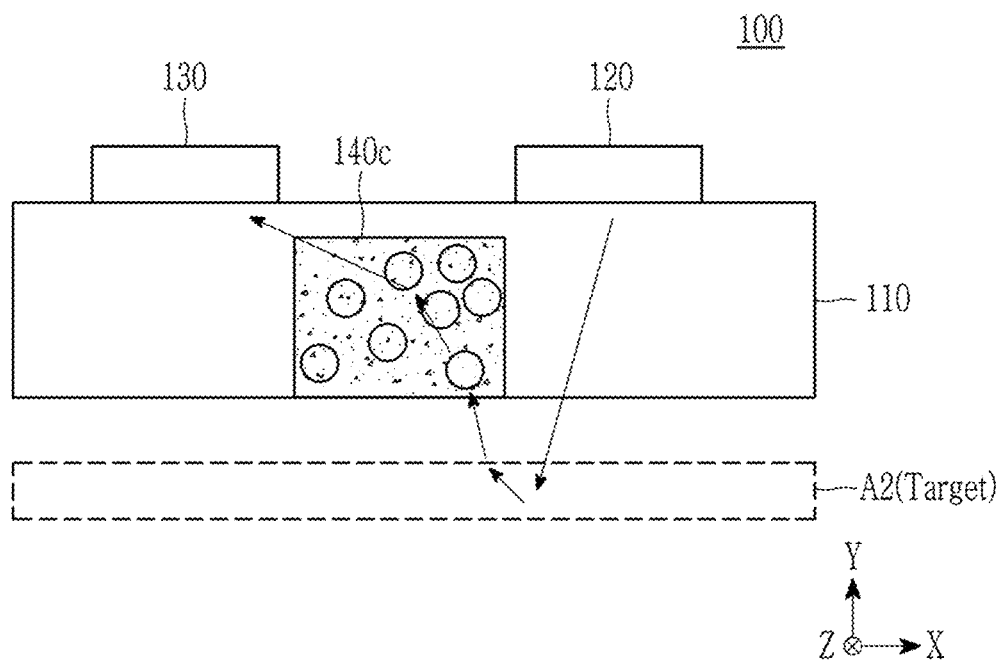
FIG. 9 is an enlarged schematic view of an example of the biosensor of FIG. 2, FIGS. 10A and 10B are schematic views showing an example of a propagation direction of light in the biosensor of FIG. 9.
Figure 10A:
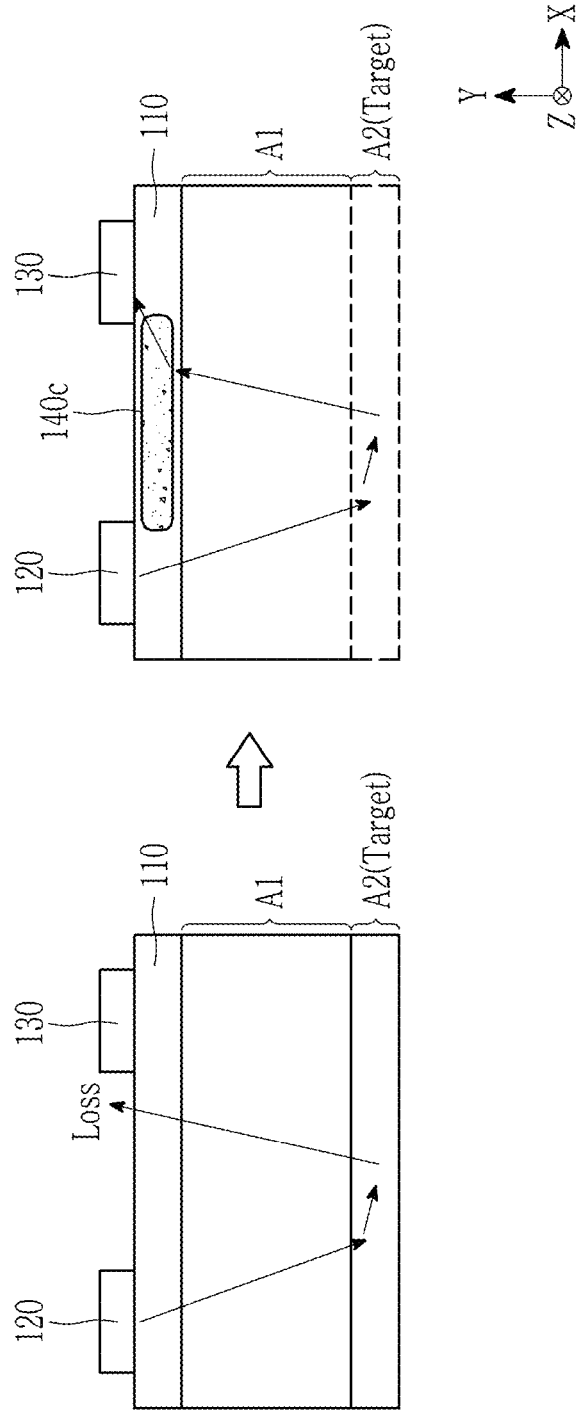
Figure 10B:
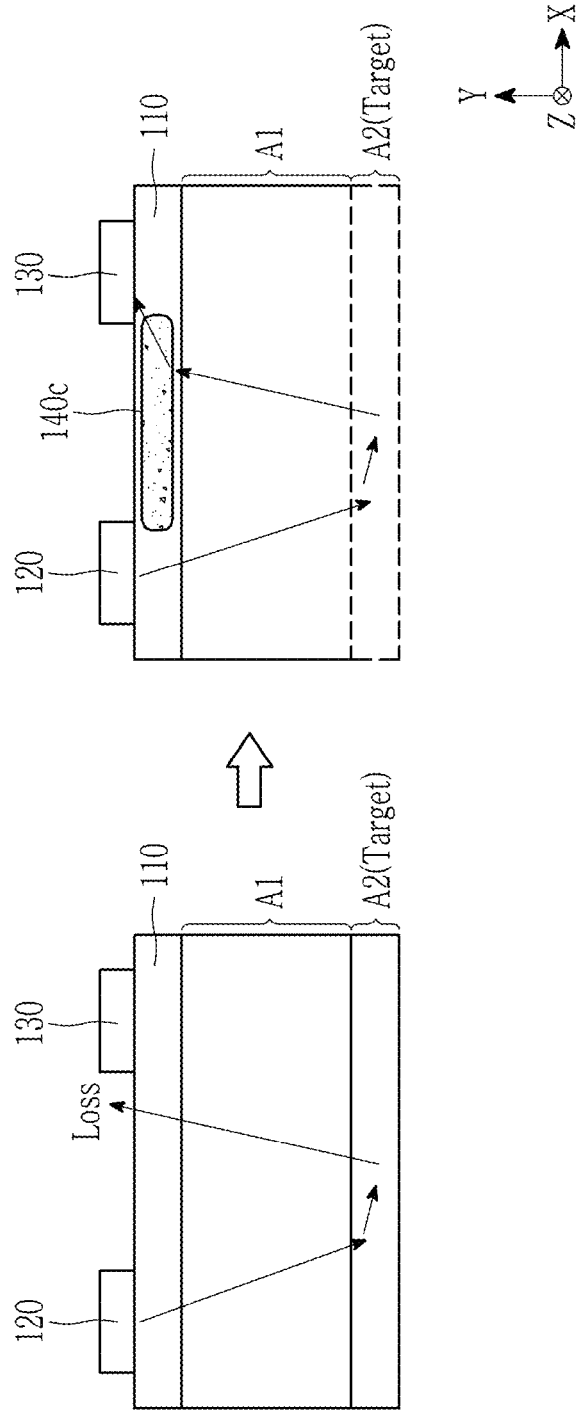

FIG. 9 is an enlarged schematic view of an example of the biosensor of FIG. 2, and FIGS. 10A and 10B are schematic views showing an example of a propagation direction of light in the biosensor of FIG. 9.

Referring to FIG. 9, the third optical structure 140c is disposed between the light-emitting element 120 and the photo-detective element 130 and thus may be configured to scatter or refract the light reflected by the target A2 such as a blood vessel and thus lead the light in a predetermined or alternatively, desired direction, for example, a direction of making the light flow into the photo-detective element 130. Accordingly, even when a gap between the light-emitting element 120 and the photo-detective element 130 is large, the third optical structure 140c may reduce or prevent the light reflected by the target A2 from being spread into the other regions excluding the photo-detective element 130 and lead the light to precisely flow into the photo-detective element 130 and resultantly, increase efficiency of the biosensor 100.

The third optical structure 140c may include a plurality of nanoparticles or porous structures to lead light in a predetermined or alternatively, desired direction. The plurality of nanoparticles may be, for example, inorganic particles, organic particles, organic/inorganic particles, or a combination thereof, for example, metal particles, metal oxide particles, metal nitride particles, or a combination thereof. The porous structures may have a plurality of pores, and may be a two-dimensional or three-dimensional structure. A particle diameter of each nanoparticle or the pore diameter in each porous structure may be several nanometers to several hundred nanometers, for example, greater than or equal to about 1 nm and less than about 1000 nm, about 1 nm to about 800 nm, about 3 nm to about 700 nm, about 5 nm to about 600 nm, or about 10 nm to about 500 nm, but is not limited to this.

As shown in FIG. 10A, when there is no third optical structure 140c, the light reflected by the target A2 such as a blood vessel may progress into the other regions excluding the photo-detective element 130, for example, a region between the light-emitting element 120 and the photo-detective element 130, while it passes the skin A1, and thus deteriorate efficiency of the biosensor 100.

Referring to FIG. 10B, the third optical structure 140c is disposed where the light reflected by the target A2 such as a blood vessel passes and thus may lead the light to continuously change the direction, while it passes a plurality of nanoparticles or pores, and to ultimately flow into the photo-detective element 130. Accordingly, the third optical structure 140c may reduce loss of the reflected light having bio-information and increase intensity of biological signals flowing into the photo-detective element 130 and thus improve efficiency of the biosensor 100.

For example, the optical structure 140 may include the aforementioned first optical structure 140a.

For example, the optical structure 140 may further include the second optical structure 140b overlapped with the photo-detective element 130 in the thickness direction (e.g., the Y direction) of the light transmitting layer 110 in addition to the first optical structure 140a. The second optical structure 140b is disposed under the photo-detective element 130 and thus may minutely control the propagation direction of light passing under the photo-detective element 130 out of the light reflected by the target A2 and reduce the light loss but increase the light inflow into the photo-detective element 130. Accordingly, the efficiency of the biosensor 100 may be increased.

For example, the optical structure 140 may include the aforementioned first optical structure 140a, second optical structure 140b, and third optical structure 140c together.

For example, the optical structure 140 may include the aforementioned third optical structure 140c.

For example, the optical structure 140 may further include the second optical structure 140b in addition to the aforementioned third optical structure 140c.

Hereinafter, a biosensor according to some example embodiments is described.

Figure 11:
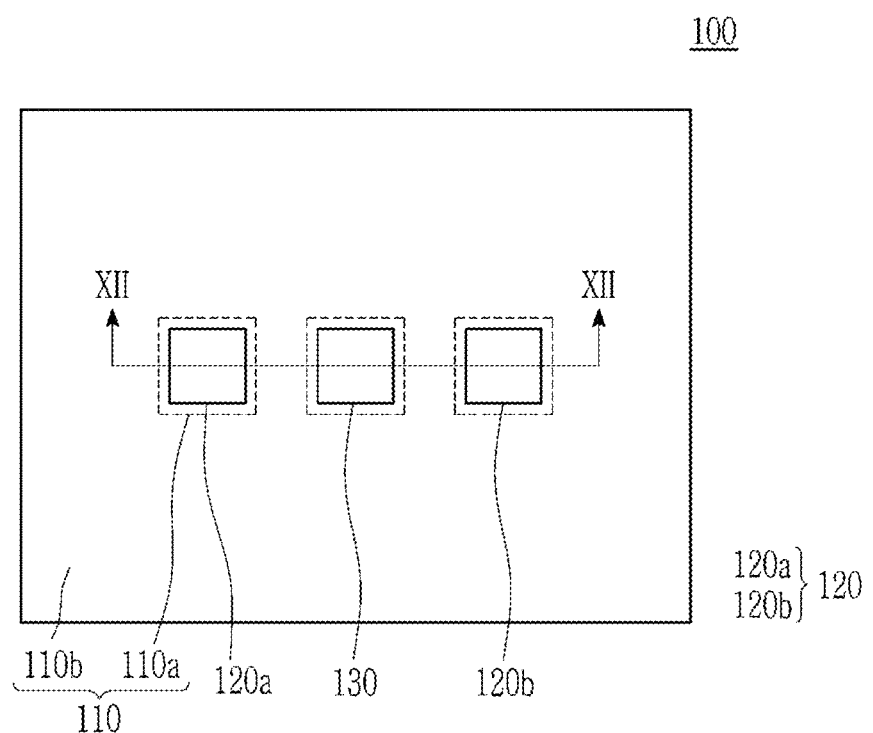
FIG. 11 is a top plan view showing another example of a biosensor according to some example embodiments.
Figure 12:
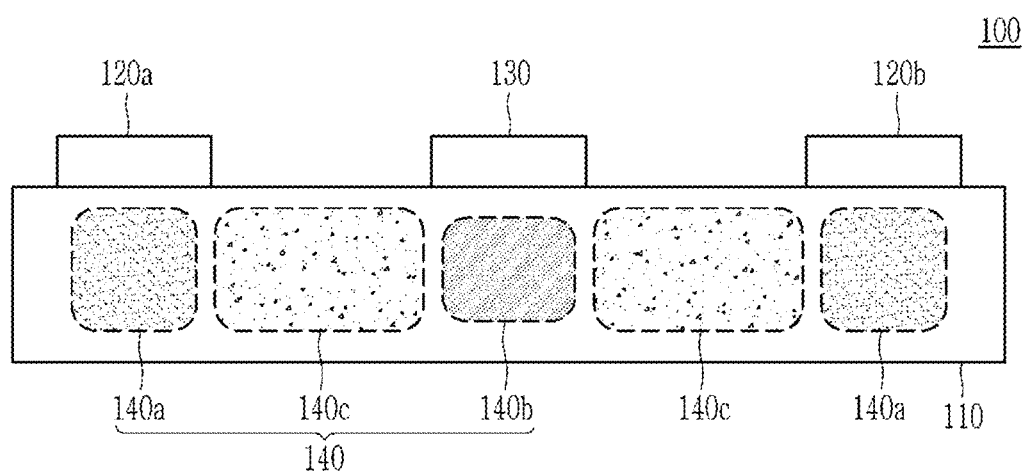
FIG. 12 is a cross-sectional view of the biosensor of FIG. 11 taken along line XII-XII.

FIG. 11 is a top plan view showing another example of a biosensor according to some example embodiments, and FIG. 12 is a cross-sectional view of the biosensor of FIG. 11 taken along line XII-XII.

Referring to FIGS. 11 and 12, the biosensor 100 according to some example embodiments includes a light-transmitting layer 110 having the first region 110a and the second region 110b, a light-emitting element 120, a light detection element 130, and/or an optical structure 140, like the aforementioned example embodiment. The detailed descriptions therefor are as described above.

However, the biosensor 100 according to some example embodiments includes a plurality of light-emitting elements 120, unlike the aforementioned example embodiment. The light-emitting element 120 includes a first light-emitting element 120a and a second light-emitting element 120b which emit light in different wavelength regions. The first light-emitting element 120a and the second light-emitting element 120b may be used to detect objects having different absorption and/or reflection characteristics. For example, the first light-emitting element 120a may be a green light-emitting element emitting light in a green wavelength region, the second light-emitting element 120b may be a red light-emitting element emitting light in a red wavelength region or an infrared light-emitting element emitting light in an infrared wavelength region. The green light-emitting element and the red/infrared light-emitting element may be, for example, used for absorption and/or reflection characteristics of oxyhemoglobin ($HbO_2$) and hemoglobin (Hb) in the blood vessel.

The aforementioned biosensor 100 may be applied in a form of an array arranged along rows and/or columns.

Figure 13:
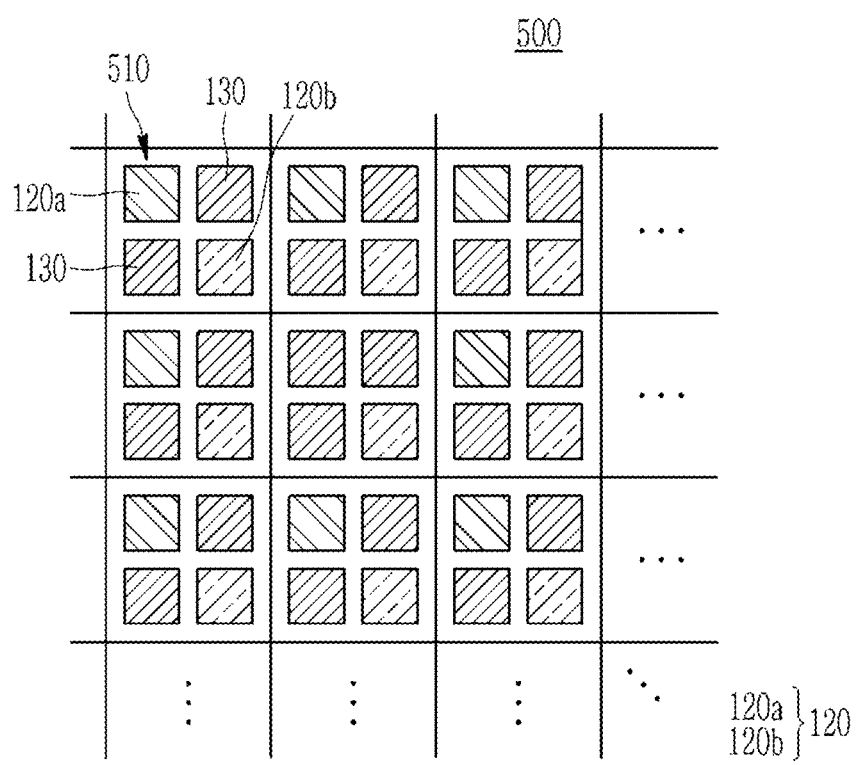
FIG. 13 is a schematic view showing an example arrangement of a biosensor array according to some example embodiments.
Figure 14:
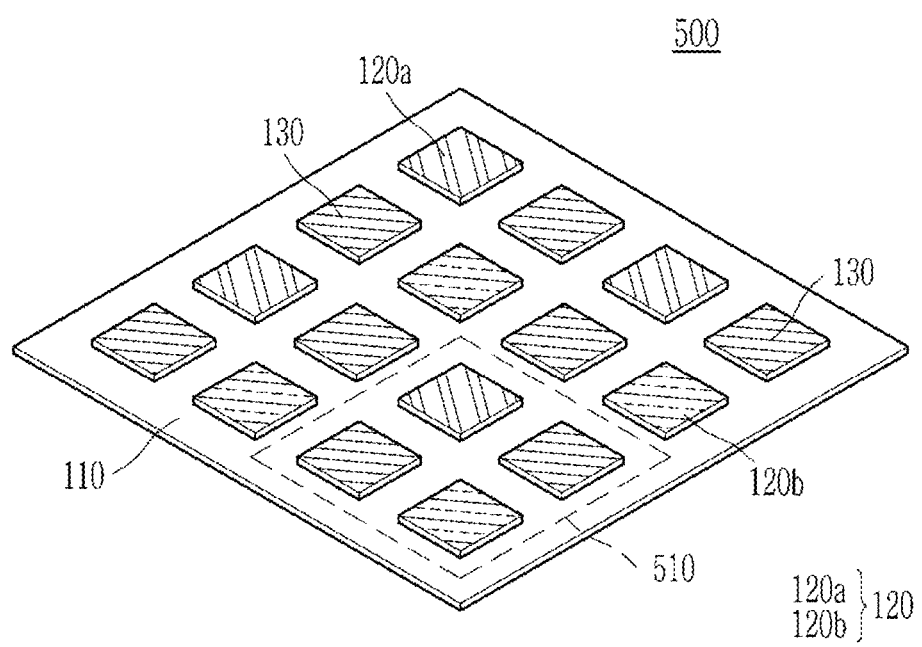
FIG. 14 is a schematic view showing a portion of the biosensor array of FIG. 13.

FIG. 13 is a schematic view showing an example arrangement of a biosensor array according to some example embodiments, and FIG. 14 is a schematic view showing a portion of the biosensor array of FIG. 13.

Referring to FIG. 13, a biosensor array 500 may have a matrix arrangement in which a plurality of unit elements 510 are repeatedly arranged along rows and/or columns. The arrangement of the unit element 510 may be, for example, a Bayer matrix, a PenTile matrix, and/or a diamond matrix, but is not limited thereto.

In the drawing, all unit elements 510 are shown to have the same size but not limited thereto, and at least one of the unit elements 510 may be larger or smaller than the other unit elements 510. In the drawing, all the unit elements 510 are shown to have the same shape but not limited thereto, and at least one of the unit elements 510 may have a different shape from those of the other unit elements 510.

Each unit element 510 may be aligned on the aforementioned light transmitting layer 110 and include the light-emitting element 120 and/or the photo-detective element 130. FIGS. 13 and 14 show that each unit element 510 includes one first light-emitting element 120a, one second light-emitting element 120b, and two photo-detective elements 130 but is not limited thereto and may include at least one of the first and second light-emitting elements 120a and 120b and at least one photo-detective element 130. Either one of the first light-emitting element 120a and the second light-emitting element 120b may be omitted.

The light-emitting element 120 and the photo-detective element 130 included in each unit element 510 may have a size (dimension) of several to hundreds of micrometers. For example, the light-emitting element 120 and the photo-detective element 130 included in each unit element 510 may independently have a width, a length, and a thickness of greater than or equal to about 1 μm and less than about 1000 μm and within the range, about 10 μm to about 800 μm, about 10 μm to about 700 μm, about 10 μm to about 600 μm, or about 10 μm to about 500 μm.

This biosensor array 500 includes the plurality of light-emitting elements 120 and the photo-detective elements 130 arranged along rows and/or columns and thus may more easily detect biological signals.

Figure 15:
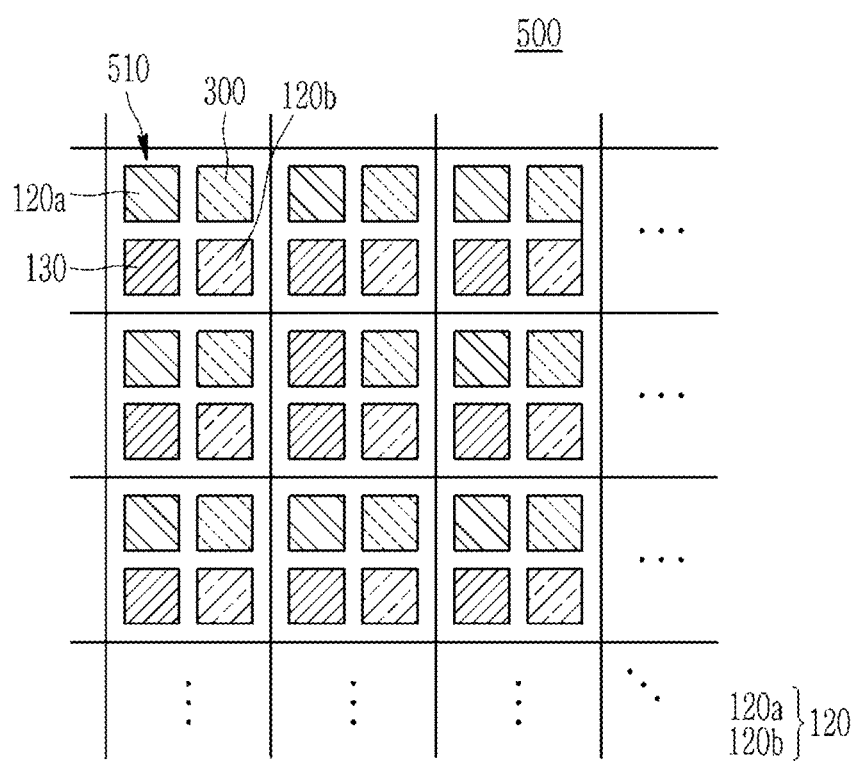
FIG. 15 is a schematic view showing an arrangement of another example of a biosensor array according to some example embodiments.
Figure 16:
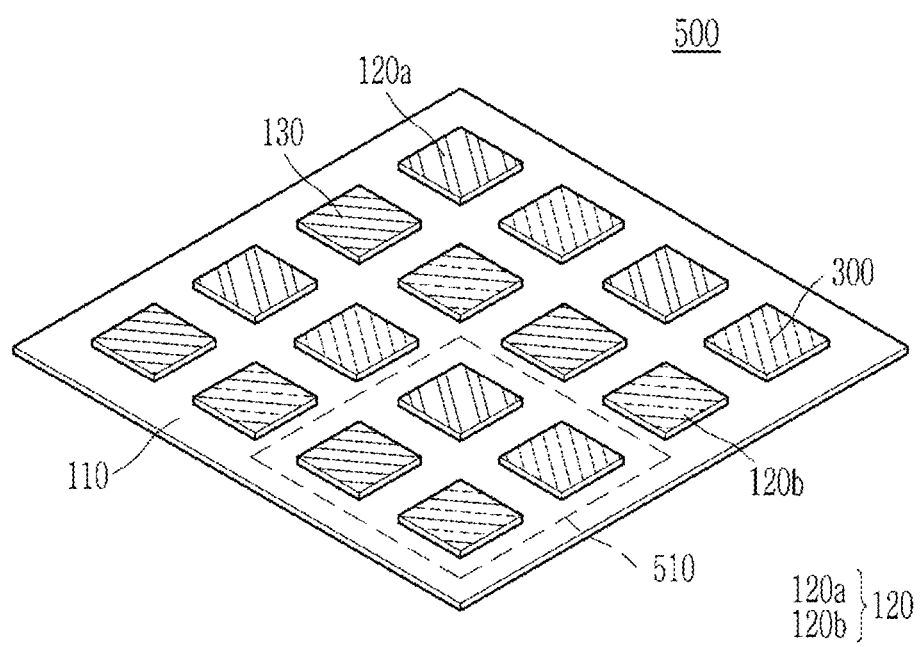
FIG. 16 is a schematic view showing a portion of the biosensor array of FIG. 15.

FIG. 15 is a schematic view showing an arrangement of another example of a biosensor array according to some example embodiments, and FIG. 16 is a schematic view showing a portion of the biosensor array of FIG. 15.

The biosensor array 500 according to some example embodiments has a matrix arrangement in which a plurality of unit elements 510 are repeatedly arranged along rows and/or columns, as in the aforementioned example embodiment, and each unit element 510 includes a light-emitting element 120 and a photo-detective element 130.

However, the biosensor array 500 according to some example embodiments further includes a pressure sensor 300 in each unit element 510, unlike the aforementioned example embodiment. That is, each unit element 510 includes a light-emitting element 120, a photo-detective element 130, and/or a pressure sensor 300. FIGS. 15 and 16 show examples that each unit element 510 includes one first light-emitting element 120a, one second light-emitting element 120b, one photo-detective element 130, and/or one pressure sensor 300 but is not limited thereto and may include at least one first and second light-emitting element 120a and 120b, at least one photo-detective element 130, and at least one pressure sensor 300. Either one of the first light-emitting element 120a and the second light-emitting element 120b may be omitted.

The pressure sensor 300 is a sensor detecting pressure changes. Accordingly, the pressure sensor 300 among a plurality of pressure sensors 300 arranged in the biosensor array 500 may be used to specify where a pressure occurs, and thus the corresponding unit element 510 alone may be selectively operated to effectively detect biological signals at the specific position of a target such as a blood vessel.

For example, a method of operating the biosensor array 500 according to some example embodiments may include, for example, specifying where the pressure sensor 300 detecting the pressure is among the plurality of unit elements 510 of the biosensor array 500 and selectively operating a unit element 510 to which the pressure sensor 300 belongs. The selective operation of the unit element 510 to which the pressure sensor 300 detecting the pressure belongs may include, for example, radiating light into the light-emitting element 120 of the unit element 510 to which the pressure sensor 300 sensing the pressure belongs and then, receiving the light reflected by the target, for example, a blood vessel from the photo-detective element 130 and converting it into electrical signals.

The aforementioned biosensor 100 or the biosensor array 500 may be applied to various devices in order to collect bio-information, for example, an attachable device such as a wearable bioelectronic device; a skin-like device; or smart clothing in order to obtain biological signals temporarily or in real time but is not limited thereto. The device may be, for example, a patch type skin-attachable device or a band type skin-attachable device.

Figure 17:
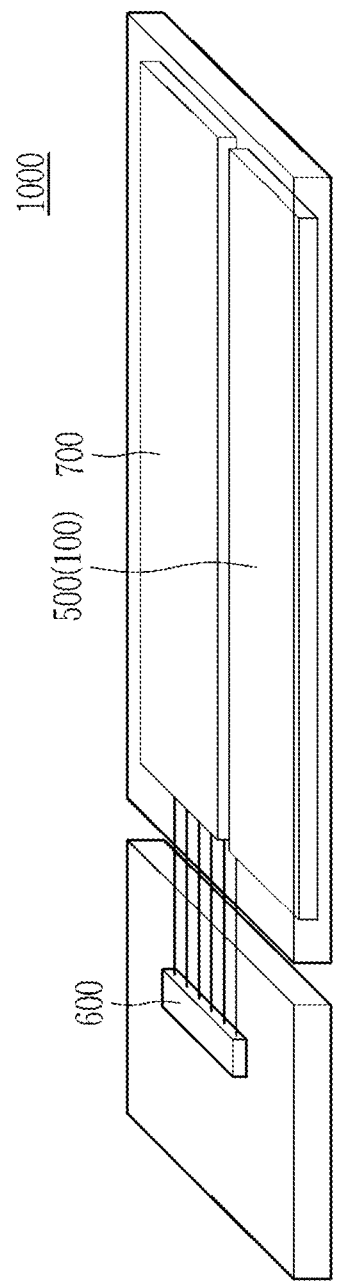
FIG. 17 is a schematic view showing an example of a device according to some example embodiments.

FIG. 17 is a schematic view showing an example of a device according to some example embodiments.

Referring to FIG. 17, a device 1000 according to some example embodiments may be a patch- or band-type attachable biosensor device and include the aforementioned biosensor 100 or the biosensor array 500; IC and/or a processor 600 for processing biological signals obtained from the biosensor 100 or the biosensor array 500 and/or a display region 700 displaying the obtained biological signals into various letters and/or images.

For example, the device may be a photoplethysmography (PPG) sensor device, an electroencephalogram (EEG) sensor device, an electrocardiogram (ECG) sensor device, a blood pressure (BP) sensor device, an electromyography (EMG) sensor device, a blood glucose (BG) sensor device, an accelerometer device, a RFID antenna device, an inertial sensor device, an activity sensor device, a strain sensor device, a motion sensor device, or a combination thereof, but is not limited thereto.

Hereinafter, example embodiments are illustrated in more detail with reference to examples. However, these examples are exemplary, and the present scope is not limited thereto.

Optical Simulation

A LightTools software is used to evaluate signal intensity of a biosensor depending on an incident angle of light emitted from a light-emitting element into a living body (a skin, a blood vessel, and the like). The incident angle is inclined toward a vertical direction (Y-axis, 0°) of the light-emitting element. The light-emitting element is based on Lambertian emitters and takes the light signals reflected by the blood vessel alone as biological signals.

The structure of the biosensor is set as follows.

Biosensor: PPG sensor

Emission spectrum of light-emitting element: 550 nm to 650 nm ($\lambda_{max}$=600 nm)

Internal quantum efficiency of photo-detective element is assumed to be 100%.

A gap between light-emitting element and photo-detective element: 0 to 1 mm

Thickness of substrate (light transmitting layer): 0.05 mm

Figure 18:
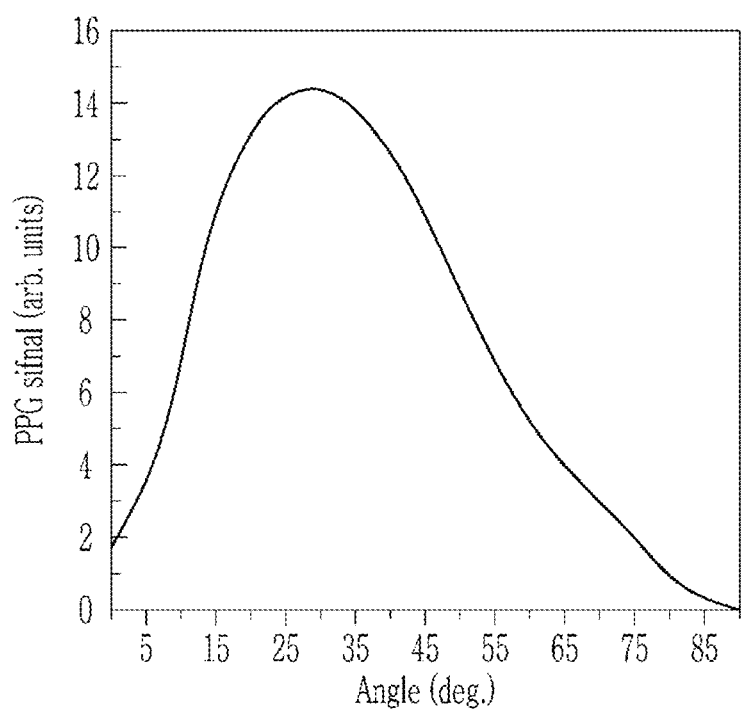
FIG. 18 is a graph showing a signal intensity of the biosensor according to the incident angle of light.

Skin: skin thickness 1.5 mm, blood vessel thickness 1 mm, fat thickness 2 mm, muscle thickness 30 mm Incidence angle on the skin (blood vessel): 0 to 90 degrees The results are shown in FIG. 18.

FIG. 18 is a graph showing a signal intensity of the biosensor according to the incident angle of light.

Referring to FIG. 18, the biosensor turns out to obtain high biological signals with respect to incident light at a predetermined or alternatively, desired angle, for example, at an angle of greater than or equal to about 10° and less than about 60°.

EXAMPLES

Example 1

A 2 mm-thick styrene-ethylene-butylene-styrene (SEBS) substrate into which a truncated circular cone-shaped Cu reflector (a long diameter: 3 mm) is inserted is prepared. Subsequently, on the SEBS substrate, a light-emitting element (BioMon Sensor, Model No.: SFH7060, OSRAM Opto Semiconductors Inc.) is disposed where the Cu reflector is overlapped, and a photo-detective element (BioMon Sensor, Model No.: SFH7060, OSRAM Opto Semiconductors Inc.)

is disposed where 4 mm away from the light-emitting element to produce a biosensor having a structure shown in FIG. 8A.

Example 2

A 1 mm-thick styrene-ethylene-butylene-styrene (SEBS) substrate into which a porous film (polyvinylidene difluoride (PVDF), reflectance>85%) is inserted is prepared. Subsequently, on the SEBS substrate, a light-emitting element is disposed at one side, and a photo-detective element is disposed at the other side to be 3 mm apart therefrom with a porous reflective film therebetween to produce a biosensor having a structure shown in FIG. 9.

Comparative Example 1

A biosensor is produced according to the same method as Example 1 except that the Cu reflector is not used.

Comparative Example 2

A biosensor is produced according to the same method as Example 2 except that the porous film is not used.

Evaluation

Performance of the biosensors according to examples and comparative examples is evaluated.

The performance of the biosensors is evaluated from a signal intensity and a signal to noise ratio (SNR).

The biosensors are attached around a radial artery of a wrist to obtain biological signals (PPG signals) and distinguish the signals (frequency between 0.5 to 10 Hz) from noises (frequency: less than 0.5 Hz and greater than 10 Hz) through Fourier transformation according to the equation, SNR=signal/noise.

The biosensors according to Example 1 and Comparative Example 1 are worn and evaluated at the same position of the wrist, and the sensors according to Example 2 and Comparative Example 2 are worn and evaluated at the same position of the wrist.

Figure 19:
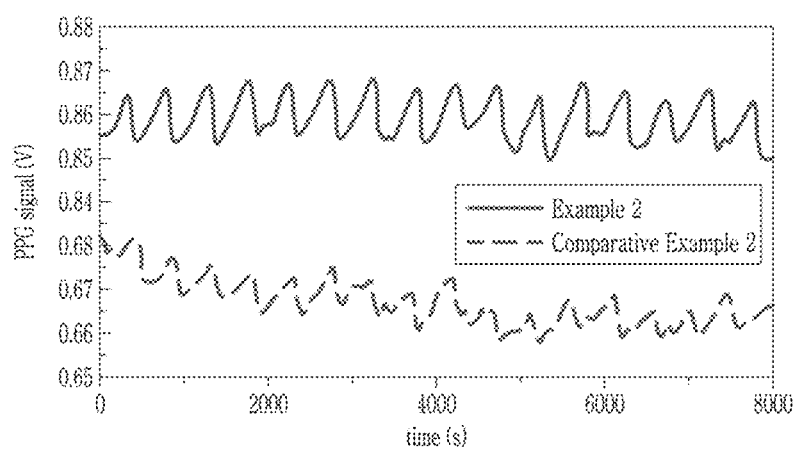
FIG. 19 is a graph showing changes of biological signals over time of the biosensors according to Example 2 and Comparative Example 2.

The results are shown in Table 1 and FIG. 19.

FIG. 19 is a graph showing changes of biological signals over time of the biosensors according to Example 2 and Comparative Example 2.

TABLE 1

|  | SNR (dB) |
| --- | --- |
| Example 1 | 15.7 |
| Comparative Example 1 | 12.7 |
| Example 2 | 21.2 |
| Comparative Example 2 | 16.6 |

Referring to Table 1 and FIG. 19, the biosensors according to Examples exhibit strong signal intensity and/or improved signal/noise ratios compared with the biosensors according to Comparative Examples.

While this disclosure has been described in connection with what is presently considered to be practical example embodiments, it is to be understood that the inventive concepts are not limited to the disclosed example embodiments. On the contrary, it is intended to cover various modifications and equivalent arrangements included within the spirit and scope of the appended claims.

What is claimed is:

1. A biosensor, comprising
a light-emitting element,
a photo-detective element,
a light transmitting layer extending continuously under the light-emitting element and the photo-detective element, and
an optical structure inside the light transmitting layer, the optical structure being configured to control a propagation direction of light passing through the light transmitting layer,
wherein the optical structure and the light transmitting layer include different materials,
wherein the light transmitting layer includes a stretchable material,
wherein the light transmitting layer includes a plurality of first regions having a higher elastic modulus and a second region having a lower elastic modulus than the plurality of first regions, wherein the second region extends between adjacent first regions of the plurality of first regions,
wherein each of the plurality of first regions has an island-shape separated from each other, and
wherein each of the light-emitting element and the photo-detective element is on a separate first region of the plurality of first regions of the light transmitting layer,
wherein the optical structure includes
a first optical structure overlapping the light-emitting element in a thickness direction of the light transmitting layer,
a second optical structure overlapping the photo-detective element in the thickness direction of the light transmitting layer, and
a third optical structure between the light-emitting element and the photo-detective element and further between the first optical structure and the second optical structure within the light transmitting layer, wherein the third optical structure is at least partially located within the second region of the light transmitting layer and is configured to scatter or refract light reflected by a living body and passing through the third optical structure in at least the second region of the light transmitting layer to direct the scattered or refracted light to the photo-detective element.

2. The biosensor of claim 1, wherein the optical structure is configured to control a propagation direction of light emitted from the light-emitting element and a propagation direction of light reflected by the living body.

3. The biosensor of claim 1, wherein the first optical structure is configured to scatter or refract light emitted from the light-emitting element.

4. The biosensor of claim 3, wherein the first optical structure is configured to control light emitted in a substantially vertical direction with respect to an in-plane direction of the light-emitting element to travel at an angle of greater than or equal to about 10 degrees with respect to the substantially vertical direction of the light-emitting element.

5. The biosensor of claim 3, wherein the first optical structure comprises a microlens or a microlens array.

6. The biosensor of claim 5, wherein an area of the microlens or the microlens array is smaller than or equal to an area of the light-emitting element.

7. The biosensor of claim 3, wherein a refractive index of a material constituting the first optical structure is different from a refractive index of a material constituting the light transmitting layer.

8. The biosensor of claim 3, wherein the first optical structure has pores.

9. The biosensor of claim 1, wherein the first optical structure is configured to reflect light emitted from the light-emitting element.

10. The biosensor of claim 9, wherein the first optical structure is configured to control reflect light emitted from the light-emitting element and to travel at an angle of less than about 60 degrees with respect to a vertical direction of the light-emitting element.

11. The biosensor of claim 9, wherein the first optical structure has a cylindrical or truncated circular conical shape.

12. The biosensor of claim 9, wherein the first optical structure comprises a metal.

13. The biosensor of claim 1, wherein the first optical structure is configured to control light emitted from the light-emitting element to travel at an angle of greater than or equal to about 10 degrees and less than about 60 degrees with respect to a vertical direction of the light-emitting element.

14. The biosensor of claim 1, wherein the third optical structure comprises a plurality of nanoparticles or porous structures.

15. A biosensor array, the biosensor array comprising a plurality of unit elements, wherein each unit element of the plurality of unit elements comprises the biosensor of claim 1.

16. The biosensor array of claim 15, wherein the each unit element further comprises a pressure sensor.

17. A device comprising the biosensor array of claim 15, wherein the device is a patch type skin-attachable device or a band type skin-attachable device.

18. A device comprising the biosensor of claim 1, wherein the device is a patch type skin-attachable device or a band type skin-attachable device.

19. A biosensor, comprising:
a light-emitting element,
a photo-detective element,
a light transmitting layer extending continuously under the light-emitting element and the photo-detective element, and
an optical structure inside the light transmitting layer, the optical structure being configured to control a propagation direction of light,
wherein the optical structure and the light transmitting layer include different materials,
wherein the light transmitting layer includes a stretchable material,
wherein the light transmitting layer includes a plurality of first regions having a higher elastic modulus and a second region having a lower elastic modulus than the plurality of first regions, wherein the second region extends between adjacent first regions of the plurality of first regions, wherein each first region and the second region are configured to transmit incident light through an entire thickness of the light transmitting layer,
wherein each of the plurality of first regions has an island-shape separated from each other, and
wherein each of the light-emitting element and the photo-detective element is on a separate first region of the plurality of first regions of the light transmitting layer,
wherein the optical structure includes
a first optical structure overlapping the light-emitting element in a thickness direction of the light transmitting layer,
a second optical structure overlapping the photo-detective element in the thickness direction of the light transmitting layer, and
a third optical structure between the light-emitting element and the photo-detective element and further between the first optical structure and the second optical structure within the light transmitting layer, wherein the third optical structure is at least partially located within the second region of the light transmitting layer and is configured to scatter or refract light reflected by a living body that is external to the biosensor such that the light is received at the biosensor from the living body in the thickness direction and is passing through the third optical structure in at least the second region of the light transmitting layer to direct the scattered or refracted light to the photo-detective element.

* * * * *